Figure 1:
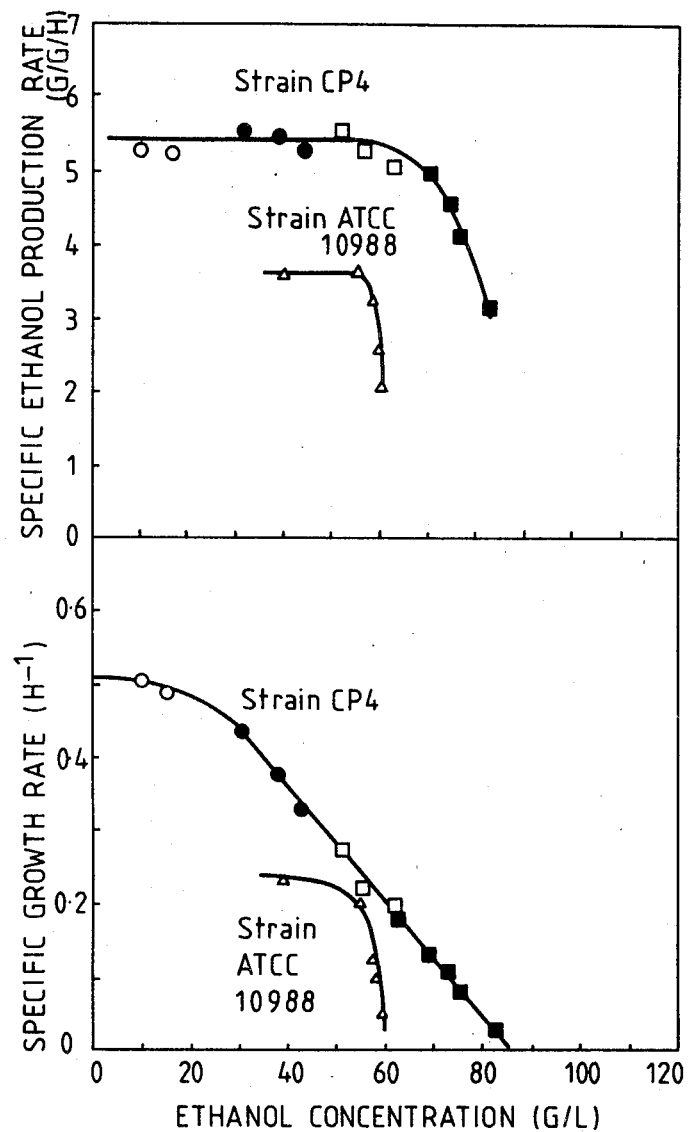

United States Patent [19]
Rogers et al.

[11] 4,403,034
[45] Sep. 6, 1983

[54] ETHANOL PRODUCTION

[75] Inventors: Peter L. Rogers, Northwood; David E. Tribe, Maroubra, both of Australia

[73] Assignee: Unisearch Limited, Kensington, Australia

[21] Appl. No.: 240,099

[22] Filed: Mar. 3, 1981

[30] Foreign Application Priority Data

Mar. 5, 1980 [AU] Australia .................. PE2655
May 15, 1980 [AU] Australia .................. PE3561

[51] Int. Cl.³ ............................................. C12P 7/06
[52] U.S. Cl. ................................. 435/161; 435/162; 435/163; 435/165; 435/813; 435/822
[58] Field of Search ............... 435/161, 162, 163, 164, 435/165, 813, 822

[56] References Cited

PUBLICATIONS

Rogers et al. "Kinetics of Alcohol Production by Zymomonas Mobilis at High Sugar Concentrations" Chem. Abstracts, vol. 91 (1979) Abstract No: 3905p.
Flickinger "Current Biological Research in Conversion of Cellulosic Carbohydrates into Liquid Fuels" Biotech & Bioeng., vol. 22 (1980) pp. 27–48.
Lee et al. "Ethanol Production by Zymomonas Mobilis in Continuous Culture at High Glucose Concentrations" Chemical Abstracts, vol. 92 (1979) Abstract No. 4686q.

Primary Examiner—R. B. Penland
Attorney, Agent, or Firm—Murray & Whisenhunt

[57] ABSTRACT

A method of producing ethanol (alcohol) comprising culturing in a suitable means a strain of *Zymomonas mobilis* which has a specific ethanol productivity at 30° C., pH5 and in a medium containing 300 g/l glucose of at least 4.0 g/g/h; a specific rate of glucose uptake at 30° C., pH5 and a medium containing 200 g/l glucose of at least 8.0 g/g/h; and an ethanol tolerance level at 30° C., pH5 and in a medium containing 300 g/l of glucose of at least 120 g/l ethanol in a batch culture or of at least 60 g/l ethanol in a continuous culture at 30° C., pH5 and in a medium containing 150 g/l glucose.

10 Claims, 1 Drawing Figure

ETHANOL PRODUCTION

The present invention consists in a process for the production of ethanol.

Ethanol is conventionally produced by the fermentation of sugars by yeasts. Such processes are used in the production of alcoholic beverages such as beer and wine. It is however also known that certain bacteria also have the ability to ferment sugars and starch hydrolysates to ethanol. One such bacteria is *Zymomonas mobilis*.

*Zymomonas mobilis* uses the Entner Doudoroff pathway for glucose metobolism and can produce up to 1.9 moles of ethanol per mole of glucose fermented. A corollary of the method by which *Zymomonas mobilis* ferments glucose is that only 1 mole of ATP is produced per mole of glucose as compared with the 2 moles of ATP produced per mole of glucose fermented by yeast using the glycolytic pathway. The lower energy available to *Zymomonas mobilis* from the fermentation process means that less biomass is produced during the fermentation process. These natural advantages have not been sufficient for *Zymomonas mobilis* to be used in large scale commercial ethanol production due to the low productivity of the previously studied strains of *Zymomonas mobilis*, their low alcohol tolerance, and their low specific rate of sugar uptake. The present inventors have been able to isolate strains of *Zymomonas mobilis* which show sufficient improvement in all three of these criteria for the use of *Zymomonas mobilis* to show advantages over the conventional yeasts for the production of ethanol. While it is surprising that even one of the criteria listed above can be markedly increased it is even more so that all three of the criteria have been able to be improved simultaneously and without any serious deleterious changes in the organism.

The present invention consists in a process for the production of ethanol from a medium containing glucose or another fermentable carbohydrate comprising culturing in the medium a strain of *Zymomonas mobilis* which has a specific ethanol productivity at 30° C., pH5 and in a medium containing 200 g/l glucose of at least 4.0 g/g/h, a specific rate of glucose uptake at 30° C., pH5 and in a medium containing 200 g/l of glucose of at least 8.0 g/g/h at 30° C. and an ethanol tolerance level at 30° C., pH5 and in a medium containing 300 g/l of glucose of at least 120 g/l ethanol in a batch culture or of at least 60 g/l ethanol in continuous cuture at 30° C., pH5 and in a medium containing 150 g/l of glucose, and recovering the ethanol so produced.

The process according to this invention may be carried out by batch culture of the microorganism or alternatively as a continuous or semi continuous process either with or without cell recycling.

The process according to the present invention is preferably carried out at a temperature of from 20° C. to 50° C., most preferably at 25° to 40° C., and at a pH between 3.7 and 8, most preferably 4.5 to 6.5. The medium preferably contains from 100 to 400 g/l of a fermentable carbohydrate, most preferably from 150 to 300 g/l.

The preferred carbohydrates for use as fermentable substrates in the culture medium include, in addition to glucose, simple sugars such as fructose, lactose and sucrose, starch and starch hydrolysates, and cellulosic raw materials. It will be recognised that any one strain of *Zymonomas mobilis* will probably not ferment all of these substrates and therefore for any particular strain a suitable, fermentable, substrate should be selected.

It is preferred that the strains of *Zymonomas mobilis* used in the process according to this invention have a specific ethanol productivity of at least 5.0 g/g/h and a specific glucose uptake of at least 10 g/g/h under the defined conditions.

The preferred strain of *Zymomonas mobilis* for use in the process according to this invention is CP4 held in the type culture collection of Prof. J. de Ley,
Laboratory of Microbiology,
Ledeganckstraat 35,
B-900 Gent
Belgium Mutants of this strain have also been found to be particularly useful in carrying out the present process and in particular have a broader range of fermentable substrates than CP4 itself. The mutant strains may be produced by mutations of an existing strain as by the use of U.V. radiation or nitrosoguanidine. Desirable properties may also be introduced into the *Zymomonas mobilis* strains by plasmid transfer from other bacteria using, for example, membrane filter mating techniques.

The strains of *Zymomonas mobilis* referred to in this specification have been deposited in the American Type Culture Collection, 12301 Park Lawn Drive Rockville, Md. 20852, U.S.A. and have been assigned the following deposit numbers and dates:

| Specification Reference | ATCC Deposit No. | Deposit Date |
| --- | --- | --- |
| CP4 | 31821 | February 26, 1981 |
| ZM481 | 31823 | February 26, 1981 |

EXAMPLES

In the following examples a comparison is made between the previously studied *Zymomonas mobilis* ATCC 10988 and the selected strain CP4 according to this invention which was originally isolated from sugar cane juice.

The strains of *Zymomonas mobilis* were first propogated at 30° C. for 24 hours without agitation by transferring single colonies from the stock culture slant to 50 ml. of preseed culture medium containing 100 g/l glucose and 10 g/l yeast extract. Ten ml of the culture broth were then transferred to 90 ml of seed culture medium. After 12-18 hours incubation, it was inoculated to 900 ml of fermentation medium containing: 100-300 g/l glucose; 10 g/l yeast extract; 1 g/l $KH_2PO_4$; 1 g/l $(NH_4)_2 SO_4$; 0.5 g/l $MgSO_4.7H_2O$. The culture was grown under non-aerated conditions at 30° C. and pH5.

Table 1 shows a comparison between the kinetic parameters of the yeast S. Cerevisiae, of *Zymomonas mobilis* ATCC 10988 and of *Zymomonas mobilis* CP4 grown under the above conditions at the stated glucose concentration.

TABLE I

| | S. Cerevisiae (ATCC 26602) | Z. Mobilis (ATCC 10988) | Z. Mobilis (CP4) |
| --- | --- | --- | --- |
| Specific Ethanol productivity, $q_p$ (g/g/h) (250 g/l glucose) | 0.87 | 2.5 | 5.4 |
| Specific glucose uptake, | 2.1 | 5.5 | 11.9 |

TABLE I-continued

|  | S. Cerevisiae (ATCC 26602) | Z. Mobilis (ATCC 10988) | Z. Mobilis (CP4) |
|---|---|---|---|
| $q_s$ (g/g/h) (250 g/l glucose) |  |  |  |
| Maximum ethanol conc. (g/l) (300 g/l glucose) | 115 | 102 | 127 |

A further comparison between the two strains is provided in FIG. 1 which shows graphically kinetic parameters for the continuous cuture of Zymomonas mobilis ATCC 10988 and Zymomonas mobilis CP4. With regard to the latter steady state results have been collected for 60, 100, 135 and 170 g/l glucose media. As is evident from FIG. 1 both the specific growth rate and the specific rate of ethanol production are higher for strain CP4 and less influenced by a given concentration of alcohol.

Another highly productive strain of Zymomonas mobilis was developed from strain CP4 as follows:

Strain CP4 was growth statically at 30° C. until it was in the exponential growth phase. Nitrosoguanidine was then added to a final concentration of 50 ug/ml and the culture was incubated for 30 minutes at 30° C. The cells were then washed twice in saline phosphate buffer and regrown overnight at 30° C. The culture was then plated on plates containing 10% (v/v) ethanol. After several days incubation at 30° C., mutant colonies appeared at a frequency of approximately $10^{-7}$, and these were purified on similar medium and then tested for growth and ethanol production rates with 100, 200 and 250 g/l glucose, at 30° C. in tubes. The culture which produced the highest level of ethanol in the shortest time was numbered ZM48.

A second similar mutagenesis was done with strain ZM48 but the cells were plated with 15% (v/v) ethanol. The mutant which produced the highest level of ethanol in the shortest time was numbered ZM481, and was kept as an ethanol tolerant strain in the type culture collection in the School of Biotechnology, University of New South Wales, Sydney, New South Wales, Australia.

Table 2 shows a comparison of maximum steady state ethanol concentrations reacted by various strains of Zymomonas mobilis in continuous culture at a dilution rate, D=0.1 hr$^{-1}$.

TABLE 2

| Strain | Glucose Conc$^n$ (g/l) | Ethanol Conc$^n$ (g/l) |
|---|---|---|
| Z. Mobilis ATCC10988 | 150 | 60 |
| Z. Mobilis CP4 | 170 | 70 |
| Z. Mobilis ZM481 | 180 | 85 |

Table 3 shows a comparison of viability of Zymomonas mobilis strains after 24 hours fermentation on 250 g/l glucose medium in batch culture.

TABLE 3

| Strain | Ethanol Conc$^n$ | % Viability |
|---|---|---|
| Z. Mobilis CP4 | 120 | 40 |
| Z. Mobilis ZM481 | 120 | 100 |

Table 4 shows by way of comparison kinetic parameters of Zymomonas mobilis ATCC 10988 and Zymomonas mobilis CP4 on various glucose media in non-aerated batch culture.

TABLE 4

| Kinetic parameters | ATCC 10988 | CP4 |
|---|---|---|
| (1) 150 g/l glucose |  |  |
| Specific glucose uptake rate $q_s$ (g/g/h) | 5.2 | 9.3 |
| Specific enthanol production rate $q_p$ (g/g/h) | 2.5 | 4.2 |
| Maximum ethanol concentration (g/l) | 77.0 | 78.0 |
| (2) 200 g/l glucose |  |  |
| $q_s$ | 5.2 | 10.4 |
| $q_p$ | 2.5 | 5.0 |
| Ethanol conc$^n$. | 100 | 105 |
| (3) 250 g/l glucose |  |  |
| $q_s$ | 5.5 | 11.9 |
| $q_p$ | 2.5 | 5.4 |
| Ethanol conc$^n$. | 102 | 117 |
| (4) 300 g/l glucose |  |  |
| $q_s$ | — | 8.1 |
| $q_p$ | — | 3.6 |
| Ethanol conc$^n$. | — | 127 |

We claim:

1. A process for the production of ethanol from a medium containing a fermentable carbohydrate substrate comprising culturing in the medium a strain of Zymomonas mobilis selected from the group consisting of CP4, ZM481, mutants thereof and mixtures thereof and which: has a specific ethanol productivity at 30° C., pH5 and in a medium containing 200 g/l glucose of at least 4.0 g/g/h; a specific rate of glucose uptake at 30° C., pH5 and in a medium containing 200 g/l of glucose of at least 8.0 g/g/h; and an ethanol tolerance level at 30° C., pH5 and in a medium containing 300 g/l of glucose of at least 120 g/l ethanol in a batch culture, or at 30° C., pH5 and in a medium containing 150 g/l of glucose of at least 60 g/l ethanol in a continuous culture, and recovering the ethanol so produced.

2. A process as claimed in claim 1 in which the strain of Zymomonas mobilis has a specific ethanol productivity at 30° C., pH5 in a medium containing 200 g/l glucose of at least 5.0 g/g/h.

3. A process as claimed in claim 1 or claim 2 in which the strain of Zymomonas mobilis has a specific glucose uptake at 30° C., pH5 and in a medium containing 200 g/l glucose of at least 10 g/g/h.

4. A process as claimed in claim 3 in which the strain of Zymomonas mobilis is ZM481.

5. A process as claimed in claim 1 in which the substrate is selected from the group comprising glucose, lactose, fructose and sucrose, starch and cellulose hydrolysates.

6. A process as claimed in claim 1, 2 or 5 in which the strain of Zymomonas mobilis is ZM481.

7. A process as claimed in claim 1 in which the strain of Zymomonas mobilis is CP4.

8. A process as claimed in claim 1 in which the process is carried out as a batch or semi-batch process.

9. A process as claimed in claim 1 in which the process is carried out as a continuous or semi-continuous process.

10. A biologically pure culture of the microorganism ZM481, being a strain of Zymomonas mobilis ATCC #31823, said culture being capable of producing ethanol upon fermentation in an aqueous nutrient medium containing an assimilable source of sugar.

* * * * *